United States Patent [19]

Benjamin

[11] Patent Number: 5,153,216
[45] Date of Patent: Oct. 6, 1992

[54] METHOD FOR TREATING CHEST PAIN

[75] Inventor: Stanley B. Benjamin, Rockville, Md.

[73] Assignee: Georgetown University, Washington, D.C.

[21] Appl. No.: 751,807

[22] Filed: Aug. 30, 1991

[51] Int. Cl.⁵ .......................................... A61K 31/415
[52] U.S. Cl. .................................................. 514/397
[58] Field of Search ........................................ 514/397

[56] References Cited
PUBLICATIONS

Chem. Abst. 113-109747b (1990).

*Primary Examiner*—S. J. Friedman
*Attorney, Agent, or Firm*—Millen, White & Zelano

[57] ABSTRACT

The known compound 1,2,3,9-tetrahydro-9-methyl-3-[(2-methyl-1H-imidazol-1-yl)methyl]4H-carbazol-4-one, which is available commercially as the dihydrate of its hydrochloride acid addition salt, is useful for the treatment of chest pain not associated with a cardial or esophageal structural abnormality, e.g., esophagael immobility.

10 Claims, No Drawings

METHOD FOR TREATING CHEST PAIN

This invention relates to a new medical use for the known compound 1,2,3,9-tetrahydro-9-methyl-3-[(2-methyl-1H-imidazol-1-yl) methyl]-4H-carbazol-4-one.

U.S. Pat. No. 4,695,578, discloses a class of 3-imidazolylmethyltetrahydrocarbazolones which may be represented by the general formula (I)

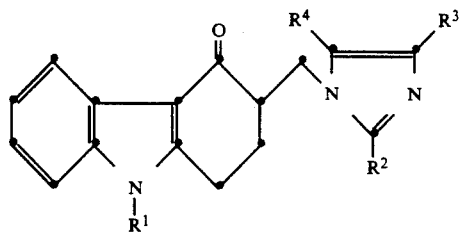

wherein $R^1$ represents a hydrogen atom or a $C_{1-10}$alkyl, $C_{3-7}$cycloalkyl, $C_{3-7}$cycloalkyl-($C_{1-4}$)alkyl, $C_{3-6}$alkenyl, $C_{3-10}$alkynyl, phenyl or phenyl-$C_{1-3}$alkyl group, and one of the groups represented by $R^2$ and $R^3$ is a hydrogen atom or a $C_{1-6}$alkyl, $C_{3-7}$cycloalkyl, $C_{2-6}$alkenyl or phenyl-$C_{1-3}$alkyl group and each of the other groups; which may be the same or different, represents a hydrogen atom or a $C_{1-6}$alkyl group; and physiologically acceptable salts and solvates, e.g. hydrates thereof.

U.S. Pat. No. 4,695,578 also discloses that physiologically acceptable compounds which are converted in vivo into the parent compound of formula (I), are physiologically acceptable equivalents of the compounds of the formula (I), e.g., physiologically acceptable thereof.

Suitable physiologically acceptable salts of the carbazolones of general formula (I) include acid addition salts formed with organic or inorganic acids for example, hydrochlorides, hydrobromides, sulphates, phosphates, citrates, fumarates and maleates. The solvates may, for example, be hydrates.

The compounds of formula (I) are described in U.S. Pat. No. 4,753,789, as potent and selective antagonists of 5-hydro-tryptamine (5-HT) at "neuronal" 5-HT receptors of the type located on terminals of primary afferent nerves, and which are also believed to be present in the central nervous system. The compounds are described in U.S. Pat. No. 4,695,578, as being of use in the treatment of a human or animal subject suffering from a condition caused by a disturbance of neuronal 5HT function, for example in the treatment of a human subject suffering from migraine pain or a psychotic disorder such as schizophrenia. It is also stated that the compounds may be useful in the treatment of conditions such as anxiety, obesity and mania.

U.S. Pat. No. 4,753,789 discloses that the compounds of formula (I) also promote gastric emptying and are anti-emetic and claims a method of treatment for the relief of nausea and vomiting, and/or the promotion of gastric emptying, e.g., for the relief of gastro-intestinal disorders associated with gastric stasis, which comprises administering to a human or animal subject an effective amount of a compound of formula (I), or a physiologically acceptable salt or solvate thereof.

SUMMARY OF THE INVENTION

It has now been found that 1,2,3,9-tetrahydro-9-methyl-3-[(2-methyl-1H-imidazol-1-yl) methyl]4H-carbazol-4-one, a compound of formula (I), and particularly a physiologically acceptable salt thereof described hereinabove (collectively referred to hereinafter as "TMMIMC"), is useful in the treatment of chest pain which is not attributable to coronary or esophageal structural diseases, which are the most common sources of chest pain, e.g., esophageal dismobility.

DETAILED DISCLOSURE

The aforesaid TMMIMC is available as its hydrochloride dihydrate from Zofran-Glaxo, Inc., Research Triangle, N.C. under the trademark "Ondansetron".

Patients with chest pain of undetermined etiology (CPUE) represent a difficult medical management problem. Visceral nociceptive abnormalities have been suggested in the prior art as contributing to chest pain (CP) in some of these patients, although conclusive evidence is lacking. Although, it is known that thoracic visceral pain is mediated by 5HT3 receptors, it was heretofore believed that non-structural abnormality related pain could only be relieved by high doses of conventional analgesics or by finding and correcting the physiological abnormality which was assumed to exist and which was the source of the pain.

This invention is based on the discovery that although "TMMIMC" is not useful as an analgesic for most types of pain, it can provide dramatic relief from or amelioration of CPUE by "abnormal visceral nonceception"which apparently does not relate to classic pain pathways. Instead, TMMIMC apparently interferes with pain perception by not having analgesic or pain control properties.

The individuals who are treated according to the method of this invention have no diagnosed structural diseases of their esophagus or heart that are normally associated with production of pain. It is believed that these individuals have a "reset" of their pain sensors such that normal activity produces what is perceived by the patient as pain. It is in that context of a resetting of the pain threshold that led to the discovery that TMMIMC, a 5HT3 receptor antagonist, works by normalizing the individual's response to physiologic activity, such as eating or exercise, which often produce these pain syndromes.

Chest pain is known to be reliably induced by intra-esophageal balloon distention (IEBD). Using this technique as a model, the ability of TMMIMC to relieve CPUE was confirmed in a randomized, placebo controlled study of Ondansetron (ON) in the alteration of IEBD-induced chest pain.

Pharmaceutical compositions for use in accordance with the present invention may be formulated in conventional manner using one or more physiologically acceptable carriers or excipients.

Thus TMMIMC in free base form and its physiologically acceptable salts and solvates may be formulated for oral, buccal, parenteral or rectal administration or in a form suitable for administration by inhalation or insufflation (either through the mouth or the nose).

For oral administration, the pharmaceutical compositions may take the form of, for example, tablets or capsules prepared by conventional means with pharmaceutically acceptable excipients such as binding agents, (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycolate); or wetting agents (e.g. sodium lauryl sulphate). The tablets may be coated by methods well known in the art. Liquid preparations for oral administrations may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavoring, coloring and sweetening agents as appropriate.

Preparations for oral administration may be suitable formulated to time controlled release of the TMMIMC.

For buccal administration the compositions may take the form of tablets or lozenges formulated in conventional manner.

TMMIMC may be formulated for parenteral administration by injection e.g. by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g. sterile pyrogen-free water, before use.

TMMIMC may also be formulated in rectal compositions such as suppositories or retention enemas, e.g., containing conventional suppository bases such as cocoa butter or other glycerides.

In addition to the formulations described previously, TMMIMC may also be formulated as a depot preparation. Such long acting formulations may be preparation. Such long acting formulations may be administered by implantation (for example subcutaneously or intramuscularly) or by intramuscular injection. Thus, for example, TMMIMC may be formulated with suitable polymeric or hydrophobic materials (for example as an emulsion in an acceptable oil) or ion exchange resins, or as sparingly soluble derivatives, for example, as a sparingly soluble salt.

For administration by inhalation TMMIMC is conveniently delivered in the form of an aerosol spray presentation from pressurized packs or a nebulizer, with the use of a suitable propellant, e.g., dichlorodifluoromethane, tri-chlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of TMMIMC and a suitable powder base such as lactose or starch.

The compositions may, if desired, be presented in a pack or dispenser device which may contain one or more unit dosage forms containing the TMMIMC. The pack may, for example, comprise metal or plastic foil, such as a blister pack. The pact or dispenser device may be accompanied by instructions for administration.

A proposed dose of TMMIMC for administration to an individual of approximately 70 kg body weight is 0.05 to 20 mg, preferably 0.1 to 10 mg of TMMIMC per unit dose which could be administered, for example, 1 to 4 times per day. The dose will depend on the route of administration and the body weight of the patient. It will be appreciated that it may be necessary to make routine variations to the dosage depending on the age and weight of the patient as well as the severity of the condition to be treated.

For oral administration a unit dose will preferably contain from 0.5 to 8 mg of TMMIMC. A unit dose for parenteral administration will preferably contain 0.1 to 8 mg of the active ingredient.

Aerosol formulations are preferably arranged so that each metered dose or "puff" delivered from a pressurized aerosol contains 0.2 mg to 4 mg of TMMIMC and each dose administered via capsules and cartridges in an insufflator or an inhaler contains 0.2 to 20 mg of TMMIMC. The overall daily dose by inhalation will be within the range 0.4 to 80 mg. Administration may be several times daily, for example from 2 to 8 times, giving for example, 1, 2 or 3 doses each time.

TMMIMC may be administered in combination with other therapeutic agents, for example a conventional analgesic to relieve associated "sympathetic" or stress pain, e.g., headache, a tranquilizer to ameliorate the anxiety of pain anticipation, an antacid, and/or a muscle relaxant.

Thus, TMMIMC may be presented together with another therapeutic agent as a combined preparation for simultaneous, separate or sequential use. Such a combined preparation may be, for example, a twin-pack. In general, the presently available dosage forms of such auxiliary therapeutic agents will be suitable for use in such combined preparations.

It will be appreciated that the TMMIMC employed in the process of this invention may be used prophylactically and references in this specification to treatment include prophylactic treatment as well as the alleviation of acute symptoms.

TMMIMC may be prepared by the process described in U.S. Pat. No. 4,695,578.

The efficacy of TMMIMC in relieving CPUE has been demonstrated in the standard human model as described herein.

Without further elaboration, it is believed that one skilled in the art, can using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all applications, patents, and publications, cited above and below, are hereby incorporated by references.

EXAMPLE

Methods

Patients with chest pain, in the absence of significant coronary artery disease or structural esophageal disease, referred to Georgetown Hospital's Esophageal Studies Lab for manometric evaluation were asked to participate in this study. The absence of significant epicardial artery disease was documented by coronary angiography. Structural esophageal disease was excluded by barium esophogram or esophogastroduodenoscopy. After consent was obtained, each patient underwent standard esophageal motility testing which included a baseline manometry, IEBD, modified Bernstien test and drug provocation with edrophonium.

Following the standard manometric evaluation patients were randomized to the sequence of Sham distention and IEBD. Balloon distention was performed using a standard eight lumen polyvinyl motility catheter (Arndorfer, Inc., Greendale, Wis.) adapted with a latex balloon (Baxter-Edwards, Inc., Irvine, Cal.). Sham distention or IEBD was performed using a three way stop cock. Patients were blinded to Sham distention and IEBD, as well as to drug and placebo, Normal Saline (NS), infusion. First, a 50 cc bolus of NS was infused intravenously over 15 minutes and after an additional 15 minutes Sham distention and IEBD were performed as per randomization. Then an intravenous bolus of Ondansetron (Zofran-Glaxo), Inc., Research Triangle Park, NC) at a dosage of 0.15 mg/kg of body weight diluted in 50 cc of NS was infused over 15 minutes and after an additional 15 minutes Sham distention and IEBD were repeated as per randomization. Volume and diameter of balloon distention, patient vital signs and symptomatic response to Sham distention and IEBD were recorded with a concurrent motility tracing. 12 lead ECG recordings were obtained at baseline and with all episodes of chest pain. A station pull-through of the LES and 5 wet swallows were performed after the Ondansetron infusion. Patients were observed for 1-2 hours and discharged ambulatory, asymptomatic and with stable vital signs.

RESULTS

In this preliminary trial, nine of ten eligible patients consented to participate, of which eight (8) had complete evaluations. Compared to placebo (NS) infusion, 6/8 patients required an increased volume of IEBD to elicit chest pain after Ondansetron infusion. One patient had a decrease in the volume of IEBD needed to elicit chest pain. Overall this group of eight patients require an average increase in IEBD volume of 2.9 cc or 29% greater than the baseline volume (see Table 1) to elicit chest pain. No significant side effects related to Ondansetron were observed.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for the treatment of chest pain which is not due to cardial or esophagal structural disease, which comprises administering to a human subject in need thereof an effective amount for treatment or the amelioration of the pain of 1,2,3,9-tetrahydro-9-methyl-3 -[(2-methyl-1H-imidazol-1-yl)methyl]-4H-carbazol-4-one or a physiologically acceptable salt or solvate thereof.

2. A method according to claim 1, wherein the 1,2,3,9-tetrahydro-9-methyl-3-[(2-methyl-1H-imidazol-1-yl) methyl]-4H-carbazol-4-one is in the form of an acid addition salt thereof.

3. The method according to claim 2, wherein the acid addition salt is the hydrochloride.

4. A method according to claim 1, wherein the 1,2,3,9-tetrahydro-9-methyl-3-[(2-methyl-1H-imidazol-1-yl) methyl]-4H-carbazol-4-one is in the form of its hydrochloride dihydrate.

5. A method according to claim 1, wherein said pain is induced by esophageal dismobility.

6. A method according to claim 5, wherein the 1,2,3,9-tetrahydro-9-methyl-3-[(2-methyl-1H-imidazol-1-yl) methyl]-4H-carbazol-4-one is in the form of an acid addition salt thereof.

7. The method according to claim 6, wherein the acid addition salt is the hydrochloride.

8. A method according to claim 5, wherein the 1,2,3,9 tetrahydro-9-methyl-3-[(2-methyl-1H-imidazol-1-yl) methyl]-4H-carbazol-4-one is in the form of its hydrochloride dihydrate.

9. The method according to claim 1, wherein the administration is intravenous.

10. The method according to claim 8, wherein the administration is intravenous.

* * * * *

UNITED STATES PATENT AND TRADEMARK OFFICE
CERTIFICATE OF CORRECTION

PATENT NO. : 5,153,216

DATED : October 6, 1992

INVENTOR(S) : Stanley B. BENJAMIN

It is certified that error appears in the above-identified patent and that said Letters Patent is hereby corrected as shown below:

```
Abstract, Line 5: Change "cardial" to - -cardiac--
Column 6,
Claim 1, Line 2:  Change "cardial" to --cardiac--
```

Signed and Sealed this

Twenty-sixth Day of October, 1993

*Attest:*

BRUCE LEHMAN

*Attesting Officer*   *Commissioner of Patents and Trademarks*